US008208983B2

(12) United States Patent
Anderson et al.

(10) Patent No.: US 8,208,983 B2
(45) Date of Patent: Jun. 26, 2012

(54) CLINICAL APPLICATIONS OF $StO_2$ ANALYSIS

(75) Inventors: LeAnn Anderson, Glencoe, MN (US); Dean E. Myers, Stewart, MN (US); Joseph P. Ortner, Hutchinson, MN (US); Gregory L. Wheatley, Hutchinson, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 1365 days.

(21) Appl. No.: 11/679,592

(22) Filed: Feb. 27, 2007

(65) Prior Publication Data
US 2007/0203406 A1     Aug. 30, 2007

Related U.S. Application Data

(60) Provisional application No. 60/777,741, filed on Feb. 27, 2006.

(51) Int. Cl.
*A61B 5/1455* (2006.01)
*A61B 5/00* (2006.01)

(52) U.S. Cl. .................... 600/323; 600/300; 600/324

(58) Field of Classification Search .............. 600/322, 600/323, 324, 310, 326, 328, 300
See application file for complete search history.

(56) References Cited

U.S. PATENT DOCUMENTS

| | | | | |
|---|---|---|---|---|
| 5,251,632 | A | * | 10/1993 | Delpy ............................. 600/323 |
| 5,385,143 | A | * | 1/1995 | Aoyagi ........................... 600/310 |
| 5,482,035 | A | * | 1/1996 | Paloheimo ..................... 600/310 |
| 5,865,736 | A | * | 2/1999 | Baker et al. .................... 600/323 |
| 5,879,294 | A | | 3/1999 | Anderson et al. |
| 6,473,632 | B1 | | 10/2002 | Myers |
| 6,587,701 | B1 | | 7/2003 | Stranc et al. |
| 6,754,516 | B2 | * | 6/2004 | Mannheimer ................. 600/323 |
| 6,822,564 | B2 | * | 11/2004 | Al-Ali ............................ 600/322 |
| 2002/0058865 | A1 | | 5/2002 | Cheng et al. |
| 2003/0088163 | A1 | | 5/2003 | Soller |
| 2006/0258928 | A1 | | 11/2006 | Ortner et al. |

OTHER PUBLICATIONS

Wukitsch et al., "Pulse oximetry: analysis of theory, technology and practice," J Clin Monit, 1988; 4: 290-301.
Zijlstra et al., "Absorption spectra of human fetal and adult oxyhemoglobin, de-oxyhemoglobin, carboxyhemoglobin, and methmemoglobin," Clin Chem., 1991;37:1633-1638.
Myers et al., "Non-invasive method for measuring local hemoglobin oxygen saturation in tissue using wide gap second derivative near-infrared spectroscopy," Journal of Biomedical Optics (10)3, 034017. 1-034017.18, 2005.
Rhee et al., "Near-infrared spectroscopy: continuous measurement of cytochrome oxidation during hemorrhagic shock," Crit Care Med. 1997;25:166-170.
Beilman et al., "Near-infrared spectroscopy measurement of regional tissue oxyhemoglobin saturation during hemorrhagic shock," Shock. 1999;12:196-200.
Crookes et al., "Noninvasive muscle oxygenation to guide fluid resuscitation after traumatic shock," Surgery. 2004; 1.35662-670.

(Continued)

*Primary Examiner* — Eric Winakur
*Assistant Examiner* — Chu Chuan (JJ) Liu
(74) *Attorney, Agent, or Firm* — Faegre Baker Daniels LLP (57) ABSTRACT

Embodiments of the invention provide a method and apparatus for using $StO_2$ values to predict an outcome of a subject's health status.

31 Claims, 12 Drawing Sheets

OTHER PUBLICATIONS

Cairns et al., "Evidence for early supply independent mitochondrial dysfunction in patients developing MODS after trauma," J Trauma. 1997;42:532-536.

McKinley et al., "Tissue hemoglobin 02 saturation during resuscitation of traumatic shock monitored using near infrared spectrometry," J.Trauma. 200 ;48:637-642.

Crookes et al., "Can near-infrared spectroscopy identify the severity of shock in trauma patients?" In press.

Jobsis, "Noninvasive, infrared monitoring of cerebral and myocardial oxygen sufficiency and circulatory parameters," Science. 1977;198:1264-1267.

Severingaus et al., "History of blood gas analysis. VI Oximetry." J Clin Monit. 1986;2:270-288.

Tremper et al., "Pulse oximetry," Anesthesiology. 1989;70:98-108.

Grotz et al., "Scoring of multiple organ failure after severe trauma: comparison of the Goris, Marshall and Moore scores," Chirurg. 2001;72:723-730.

Cumming et al., "Objective estimates of the incidence and consequences of multiple organ dysfunction and sepsis after burn trauma," J Trauma. 2001;50:510-515.

Fitzwater et al., "The risk factors and time course of sepsis and organ dysfunction after burn trauma," J Trauma. 2003;54:959-966.

Cook et al., "Multiple organ dysfunction: baseline and serial component scores," Cri Care Med. 2001;29:2046-2050.

Marshall et al., "Multiple organ dysfunction score: a reliable descriptor of a complex clinical outcome," Crit Care Med. 1995; 23:1638.

International Search Report and Written Opinion of international application No. PCT/US07/62868, mailed Feb. 21, 2008, 7 pp.

* cited by examiner

The probability of developing MODS as a function of *MinStO₂*, based on logistic regression modeling, is shown in Figure 13

CLINICAL APPLICATIONS OF STO$_2$ ANALYSIS

CLAIM OF PRIORITY

This application claims the benefit of provisional application Ser. No. 60/777,741, filed Feb. 27, 2006.

TECHNICAL FIELD

The present invention relates to a method for acquiring and characterizing data relating to tissue oxygenation. More particularly, the present invention relates to a method of determining subject status based on data relating to tissue oxygenation.

BACKGROUND OF THE INVENTION

Septic shock is the most serious complication of sepsis, a disorder that occurs when the body responds to an infection. Shock, including septic shock, is characterized by blood flow that is inadequate to meet tissue oxygen demand. Prompt recognition of inadequate organ and tissue blood flow, known as hypotension and hypoperfusion, is essential for timely treatment and improved outcome in shock related disorders. Thus, tissue oxygenation may be monitored as a means of predicting and diagnosing shock, sepsis and other types of infections, as well as predicting a subject's overall health.

SUMMARY OF THE INVENTION

One embodiment of the invention is a method for predicting a health status of a subject which includes measuring the levels of hemoglobin oxygenation (StO$_2$) in tissue of the subject, comparing the measured levels to a threshold value and predicting the status of the subject, wherein levels of hemoglobin oxygenation above the threshold value is associated with a first health status, and levels of hemoglobin oxygenation below the threshold value is associated with a second health status.

Another embodiment of the invention is an apparatus for predicting a subject's health status based on a measure of hemoglobin oxygenation saturation which includes a subject interface comprising a light path for irradiating tissue of the subject with spectroscopic radiation and a detector for detecting a spectral response from the tissue responsive to irradiation with the spectroscopic radiation, a display for displaying data, memory storing a predetermined threshold value limit, and a processor operatively connected to the memory and the subject interface such that the processor generates data from information comprising the spectral response of the tissue sample in a pre-selected format, the processor issuing a signal to indicate when a measured StO$_2$ data is outside of a pre-determined threshold or range.

A further embodiment of the invention is a device for predicting a subject's health status based on a measure of hemoglobin oxygen saturation including means for sensing including a light source assembly for generating spectroscopic radiation for irradiating a tissue and a spectroscopic detector for detecting a spectral response emitted by the tissue sample responsive to irradiation with the spectroscopic radiation, means for displaying data, means for providing a notice to a user upon the occurrence of a specified event, means for storing, said means for storing including a predetermined threshold or range, a means for generating data of the tissue sample from information comprising the spectral response of the tissue sample, a means for characterizing the data in a pre-selected form including a control system interfaced with the means for storing and the means for sensing such that the control system generates data of the tissue sample, and a means to indicate when a measured StO$_2$ data is outside of the pre-determined threshold or range.

Still another embodiment of the invention is a method of determining a relationship between StO$_2$ and a health status of a subject comprising,
monitoring the subject's StO$_2$ for a period;
storing the subject's StO$_2$ measurements versus time to form an StO$_2$ curve;
determining an area between the StO$_2$ curve and a threshold; and
determining whether the subject is likely to develop a first health status if the area is above the threshold or generally trending above the threshold, or likely to develop a second health status if the area is below the threshold or generally trending below the threshold.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION OF THE INVENTION

StO$_2$ is the quantification of the ratio of oxygenated hemoglobin to total hemoglobin in the microcirculation of skeletal muscle. The measurement of StO$_2$ is taken with a noninvasive, fiber optic light that illuminates tissues below the level of the skin. One way to illuminate tissue below the level of the skin is known as near infrared spectroscopy (NIRS), which uses specific, calibrated wavelengths of near infrared light to noninvasively illuminate the tissue below the skin. These wavelengths of light scatter in the tissue and are absorbed differently dependent on the amount of oxygen attached to hemoglobin in the arterioles, venules, and capillaries. Light that is not absorbed is returned as an optical signal and analyzed to produce a ratio of oxygenated hemoglobin to total hemoglobin, expressed as % $StO_2$.

In practice, near infrared light penetrates tissues such as skin, bone, muscle and soft tissue where it is absorbed by chromophores (hemoglobin and myoglobin) that have absorption wavelengths in the near infrared region (approximately 700-1000 nm). These chromophores vary in their absorbance of NIRS light, depending on changes in the oxygenation state of the tissue. Complex algorithms differentiate the absorbance contribution of the individual chromophores.

NIRS permits continuous, noninvasive measurement of tissue hemoglobin oxygen saturation and has been evaluated in a wide range of conditions. A NIRS system may be employed to noninvasively and continuously measure hemoglobin oxygen saturation at an upper extremity, shoulder, or lower extremity.

In one embodiment, The InSpectra™ Tissue Spectrometer—Model 325 (Hutchinson Technology Inc., Hutchinson, Minn.), which is a noninvasive monitoring system that measures an approximated value of percent hemoglobin oxygen saturation in tissue, may be used.

The InSpectra™ tissue spectrometer measures hemoglobin oxidation values in tissue based on spectrophotometric principles which relate light absorption to chemical concentration. Wukitsch M W, Petterson M T, Tobler D R, Pologe J A, "Pulse oximetry: analysis of theory, technology and practice," J Clin Monit., 1988; 4:290-301. The absorption spectra of oxygenated and deoxygenated hemoglobin are well characterized and provide a means to calculate percent hemoglobin saturation (% $StO_2$), Zijlstra W G, Buursma A, Meeuwsen-van der Roest W P, "Absorption spectra of human fetal and adult oxyhemoglobin, de-oxyhemoglobin, carboxyhemoglobin, and methmemoglobin," Clin Chem., 1991; 37:1633-1638.

The InSpectra™ tissue spectrometer measures tissue absorbance values at wavelengths between 680-800 nanometers. The tissue absorbance values are transformed into a scaled second derivative absorbance value to provide a tissue spectral measurement that is robust to total hemoglobin and optical path length changes. The process to transform the data to a scaled second derivative absorbance value may be performed as disclosed in U.S. Pat. No. 5,879,294 ("Anderson") or as disclosed in "Non-invasive method for measuring local hemoglobin oxygen saturation in tissue using wide gap second derivative near-infrared spectroscopy." (D. Meyers et al., Journal of Biomedical Optics, 10(3), 034017.1-034017.18 (2005). An empirically derived calibration curve which relates the scaled second derivative measured value to the displayed $StO_2$ is stored permanently within the device. Oxygenated and deoxygenated hemoglobins are included in the tissue saturation value, $(HbO_2/(HbO_2+Hb))\times 100$, to yield a functional percent saturation.

Figure 1:
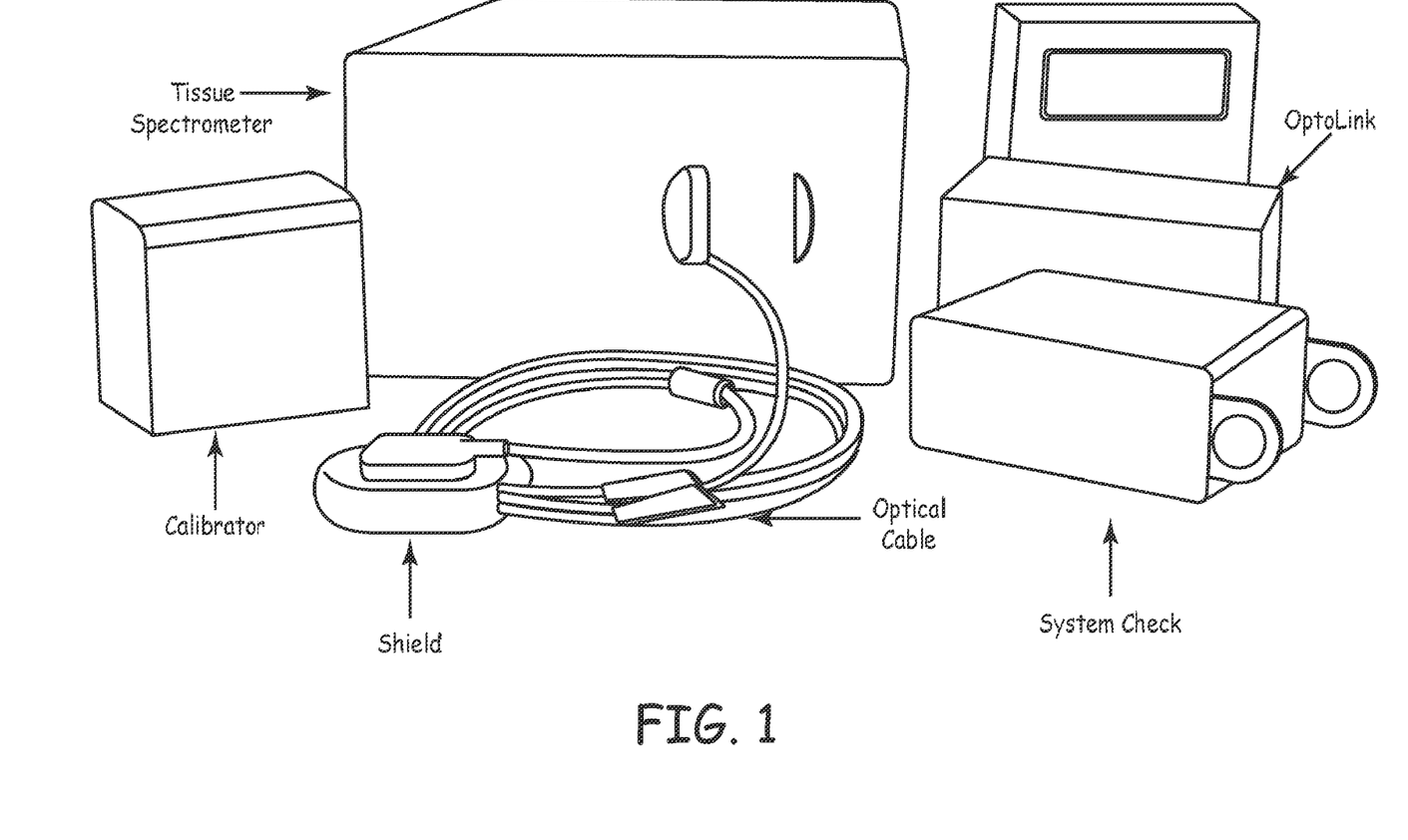
FIG. 1 illustrates the components of the InSpectra™ spectrophotometric system.
Figure 2:
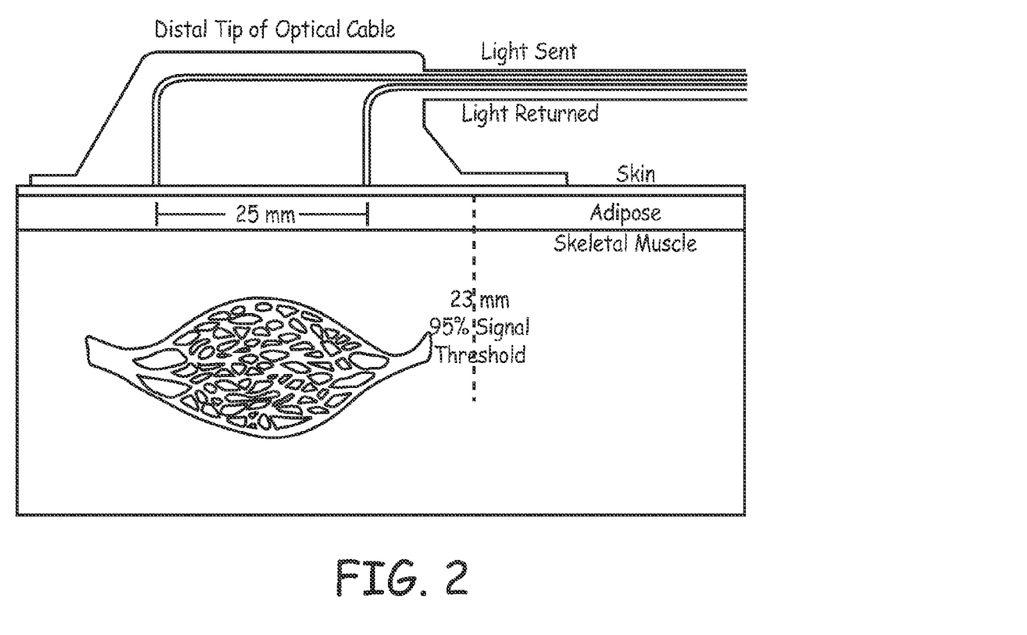
FIG. 2 schematically illustrates light transmission in tissue.

$StO_2$ is a measure of hemoglobin oxygen saturation of blood contained in the volume of tissue illuminated by the InSpectra™ tissue spectrometer. The depth of tissue measured by the InSpectra™ tissue spectrometer is directly related to the distance between the illumination fibers and detection fibers on the distal tip of the optical cable. In phantom solutions containing scattering and absorbing components proportioned to mimic well-perfused tissue, studies of spacing between illumination and detection fibers suggest that with 25 mm spacing, approximately 95% of the detected optical signal is from a depth of zero to 23 mm (See FIG. 2).

The InSpectra™ Spectrophotometer includes The InSpectra™ Optical Cable, which is a fiber optic light integration cable that contains one set of optical fibers to integrate and transmit wavelengths of light to the tissue, and a second set of optical fibers that receives light from the tissue and returns it to a photosensitive detector. Light emitting diodes in the optical cable connector are the light source.

The InSpectra™ Spectrophotometer also includes The InSpectra™ Shield, which is a disposable, soft foam pad that attaches to the distal tip of the optical cable and shields the measurement from ambient light. It is supplied with adhesive for continuous subject monitoring and with a non-adhesive liner for intermittent measurements.

The InSpectra™ Calibrator is a disposable module that normalizes the tissue spectrometer and takes a reference measurement during start-up of the system. The InSpectra™ System Check is a method to check system measurements. The InSpectra™ OptoLink™ RS232 Optical Converter is a device to export $StO_2$, date and time data from the spectrometer.

Figure 3:
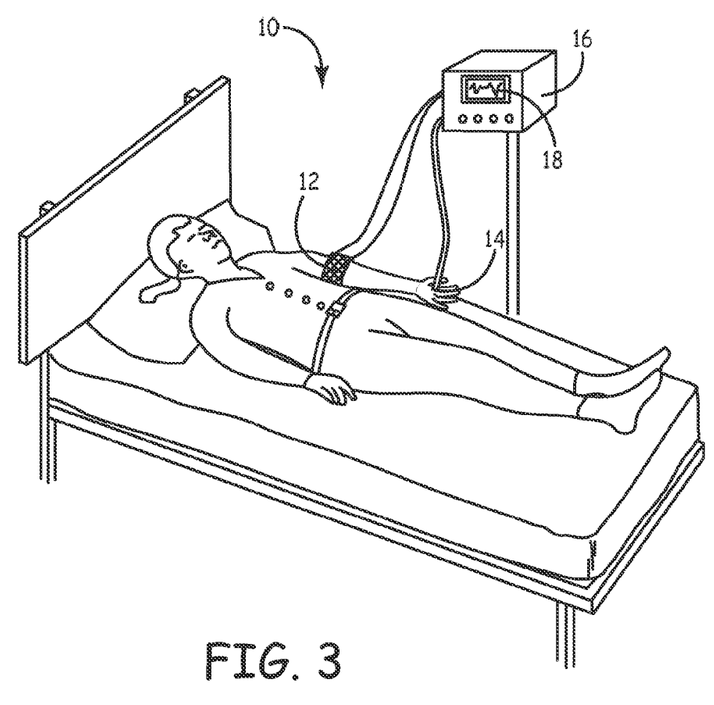
FIG. 3 shows a schematic illustration of a tissue oxygenation monitoring system that can be used in relation to embodiments of the present invention.

Another embodiment of the invention uses a system as shown in FIG. 3. System 10 is used for gathering, analyzing and displaying data related to a subject's tissue oxygenation. The information conveyed by the displayed data may be employed by a physician to monitor in real time a subject's dynamic tissue oxygenation response characteristics.

The system 10 includes a subject sensor 14 for gathering data related to tissue oxygenation of the tissue region, a control module 16 in communication with the sensor 14 for analyzing or characterizing the tissue oxygenation data, and a display 18 for indicating or displaying tissue oxygenation data.

The sensor 14 includes a noninvasive, fiber optic light that illuminates tissues below the level of the skin (not shown). In one embodiment, the sensor 14 employs near infrared spectroscopy (NIRS), which uses specific, calibrated wavelengths of near infrared light to noninvasively illuminate a region of tissue below the skin. These wavelengths of light scatter in the tissue and are absorbed differently depending on the amount of oxygen attached to a tissue chromophore, such as hemoglobin, in the arterioles, venules, and capillaries. Light that is not absorbed is returned to the sensor. Thus, the sensor 14 is able to gather data on a tissue chromophore whose light absorption properties depend on the oxygenation state of the tissue. The returned light may be transmitted as an optical signal and is analyzed to produce a ratio of oxygenated hemoglobin to total hemoglobin, expressed as % $StO_2$. Tissue chromophore data may also be expressed as tissue oxygenation, tissue deoxygenation and/or total amount of hemoglobin in the tissue. An exemplary sensor for use with the present invention is described in U.S. patent application Ser. No. 11/129,935 titled SUBJECT INTERFACE FOR SPECTROSCOPY APPLICATIONS, filed on May 16, 2005, the entire disclosure of which is hereby incorporated herein by reference.

The sensor 14 may be placed on any location. For example, the sensor 14 may be placed on the thenar muscle of the thumb, as is shown in FIG. 3. Alternately, the sensor 14 may be located on the hypothenar, the forearm, the upper arm, the deltoid, the calf, masseter muscle (cheek), etc.

Because NIRS is capable of measuring tissue oxygenation levels particular to the localized area of placement of the sensor 14, the sensor 14 may be placed in locations to monitor particular areas of interest. For example, the sensor 14 may be placed over or adjacent to areas of trauma so as to measure tissue oxygenation of the traumatized or healing tissues. The sensor 14 may also be placed over areas where infection is known or suspected to exist. The sensor 14 may also be placed in locations known to be provided with good arterial blood flow or having certain types of tissue which are more easily illuminated by the sensor 14.

The sensor 14 and control module 16 may be provided with a variety of means of communicating with one another. For example, as shown in FIG. 3, the control module 16 and the sensor 14 may be connected to one another and communicate via electrical or optical signals. In other embodiments, the connection between the control module 16 and the sensor 14 is wireless, and the control module 16 and the sensor 14 communicate with radio signals or other "wireless" modes of communication. In addition, the light source for the sensor 14 may be located either in the sensor 14 or remotely from the sensor 14 and optically coupled thereto.

The control module 16 is adapted for controlling the operation of the sensor 14, analyzing data generated by the sensor 14, and communicating data to the display 18. The control module 16 may include a data processor or other means of analyzing data communicated from the sensor 14. Furthermore, the control module 16 and display 18 may be integrated into a single unit, as shown in FIG. 3, or may be separate from one another and/or integrated into other monitoring and display devices.

The display 18 may display information relating the measured tissue oxygenation as well as characterizing data (e.g. as a cumulative ischemia score, a threshold value or minimum $StO_2$ value) based on the measured tissue oxygenation. The display of such information may take a variety of formats. For example, the display 18 may be adapted to display text, graphs or waveforms relating to contemporaneously acquired data, historical data, mean data or any combination thereof. The display 18 may also be adapted to provide instructions as to the use of the system 10 or to display notices or warnings related to the operation and functionality of system 10.

In one embodiment, the method employing the system 10 shown in FIG. 3 to analyze a subject's tissue oxygenation capabilities includes the following steps. The sensor 14 is placed on the skin in a selected region, for example, over the thenar eminence (the fleshy mass on the palmar surface of the hand at the base of the thumb) muscle of the hand. An initial measurement is taken by the sensor 14 to collect data on a tissue chromophore whose light absorption properties depend on the oxygenation state of the tissue. In one embodiment, the tissue chromophore is related to $StO_2$. The sensor 14 continues to collect data on the tissue chromophore for a predetermined time, or may simply be measured continuously for extended periods of time.

Using the data collected during the measurements, characterizing data related to the measured tissue chromophore may be automatically determined. In one embodiment, the tissue chromophore amount for the time point representing the third tissue chromophore measurement behind the leading tissue chromophore measurement is returned. This trailing chromophore measurement is predicted from a second order polynomial equation fitted to eight consecutive measurements. The returned measurement thus represents a smoothed value which is less sensitive to spurious measurements.

In another embodiment, system 10 provides a method of determining if a subject is becoming progressively healthier or closer to a normal state versus unhealthier or closer to an abnormal state. For example, a subject characteristic trending toward an abnormal or unhealthy state relative to a control population (or predetermined threshold) may be determined as progressing towards an unhealthy physiologic state. Conversely, a subject whose characteristic data is trending toward a normal or healthy state relative to a control population (or predetermined threshold) may be determined as progressing towards a healthy physiologic state. Furthermore, the rate at which the subject's characteristic data changes over time may be indicative of a normal or abnormal, healthy or unhealthy physiologic state. For example, a rapid change in a subject's $StO_2$ values trending toward an abnormal or unhealthy state may be indicative of a more serious underlying disease or defect than would a more gradual change. Thus, while consecutive measurements of the subject's $StO_2$ values may be within normal or healthy ranges, a trend in changes in the $StO_2$ values or the rate at which the $StO_2$ values is changing may be indicative of an abnormal or unhealthy state.

In another embodiment, the present invention provides a software program for characterizing a subject's oxygenation capabilities. A software program may be provided for controlling the operation of the sensor 14 as well as for inputting measurement data, determining characterizing data, and generating a display of subject data. Such a software program may be installed on a control module 16, a personal computer, processor, or other hardware as is commonly found in hospital and emergency rooms.

Figure 4:
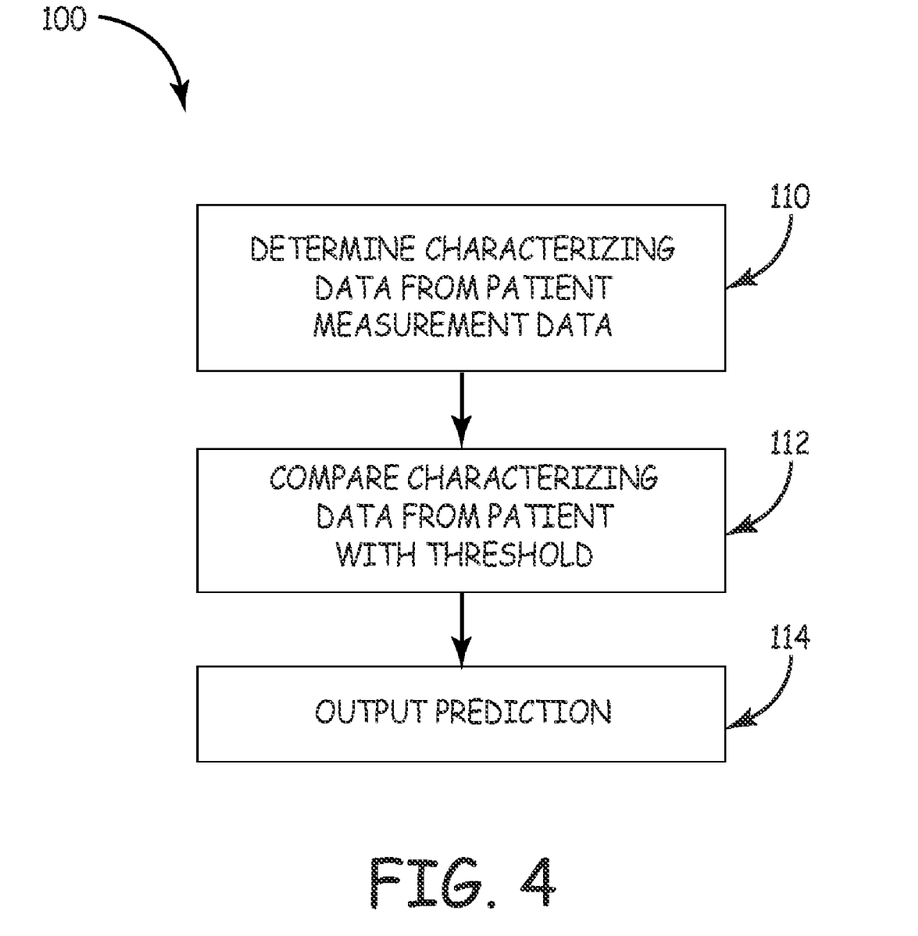
FIG. 4 is a flow chart illustrating the structure of a software program for use with an embodiment of the present invention.

FIG. 4 outlines the structure of a software program 100 for use with an embodiment of the present invention. The software program instructs the sensor 14 to take an initial measurement of a tissue chromophore whose light absorption properties depend on the oxygenation state of the tissue. Characterizing data is determined from the subject measurement data (block 110). The subject characterizing data is compared to a pre-determined threshold (block 112). A display of the subject's health prediction or status is outputted for display on a monitor or other display means (block 114).

In another embodiment, the present invention is a software program adapted for determining characterizing data from inputted subject tissue chromophore measurement data.

In one embodiment, a prognosis or health status of a subject is made based on a predetermined threshold of the $StO_2$ values. For example, it has been experimentally and clinically shown that levels of $StO_2$ that are greater than 75 percent correspond/correlate to a first health status. The first health status is predictive of a lower risk or probability of developing an adverse health outcome. In contrast, levels of $StO_2$ less than 75 percent correspond/correlate to a second health status. The second health status is predictive of a higher risk or probability of developing an adverse health outcome.

The $StO_2$ threshold limit is associated with a probability of predicting a subject's current or future health status event. Examples of a current health status event include ischemia, hypo perfusion, hypoxia, or oxygen debt. Additionally, the health status event could be associated with the abnormal or normal status of another hemodynamic measurement variable such as lactate, base deficit, or central venous hemoglobin oxygen saturation. Examples of future health status events include early death, development of multiple organ dysfunction, ventilator free days or number of hospitalization days.

The $StO_2$ threshold limit that best differentiates a positive and negative event outcome can be obtained through receiver operating curve (ROC) statistical analysis. For example, a subject's future health status can be classified as an adverse outcome and a nonadverse outcome. The optimal $StO_2$ threshold limit provides the best combination of sensitivity (for example, probability of predicting an adverse outcome) and specificity (for example, probability of predicting a nonadverse outcome) for tested Cumulative Ischemia Score (CISS) or minimum $StO_2$ cutoff values. The CISS is described further below.

In other embodiments, the $StO_2$ threshold limit is also defined as the lower $StO_2$ limit of a healthy control population. Additionally the $StO_2$ threshold limit is determined from analysis of variance (ANOVA) or student's t-test (or z or f tests) which indicate optimal statistical significance ($p$-value<0.05) for tested $StO_2$—$StO_2$ threshold values. In this case the $StO_2$ threshold variable is changed until the adverse and nonadverse groups' mean CISS becomes most statistically significant.

Additionally, a number of data processing rules (applied to individual measurements, i.e., updated every 3.5 seconds) can be used to limit the amount of non-continuous (i.e., missing) measurements, describe a desired analysis time end point or interval and/or smooth the data. Subjects must have a minimum of ten minutes of continuous data in the first hour to be considered for analysis. Subjects who do not meet this criterion are excluded from all data analyses.

To be considered analyzable, each subsequent hour of data must have a minimum of ten minutes of continuous $StO_2$ data. However, this guideline may be modified as follows in the software code: at least 10 minutes of 3.5 second $StO_2$ measurements must be present between a given study endpoint time and its closest preceding endpoint time. In some embodiments, the current analysis endpoint times are 0.5, 1, 2, 4, 6, 9, 12, 15, 18, and 24 hours. For example, to have a valid minimum $StO_2$ associated with endpoint time 4 hours, there must be 10 minutes of $StO_2$ monitoring between the 2 and 4 hour endpoints. A minimum of 13 data points must be present within a one-minute period in order to have a valid one-minute $StO_2$ reading, i.e., 75% of the possible 17 data points must be present.

A five-minute $StO_2$ reading is the running average of at least four one-minute $StO_2$ readings. As used herein, minimum $StO_2$ refers to the lowest five-minute averaged $StO_2$ reading occurring within the analysis time interval.

In one embodiment, the relationship between $StO_2$ and health status is quantified by determining the Area Under the Curve (AUC). (AUC) will be calculated using two methods: Method I measures the area below a designated threshold (negative area). Method II measures the difference between the area above the threshold and the area below the threshold (net area). Both methods also include a modified calculation which allows comparison between subjects when the time varies due to missing data. $StO_2$ thresholds of 60% and 70% were used.

AUC Method I: $StO_2$ area below the threshold (negative area) is measured at the first 30 minute time segment and at each one hour segment up to 24 hours (t=0.5, 1, 2, 3, 4 . . . 24). The calculated area is the accumulated negative area from t=0 until t=n. T=0 is the time the subject enters the emergency department, or when monitoring begins.

Modified Method I: Accumulated area is calculated at the same time points as Method I; however, the area value is indexed for time (i.e. number of measurements). Indexing for number of measurements yields a value which is an average of the $StO_2$ measurements that have occurred below the threshold up to t=n. Using this method allows comparison between individuals when the monitoring time differs.

AUC Method II: $StO_2$ area below the threshold is subtracted from the $StO_2$ area above the threshold (net area). This accumulated area is measured at the first 30 minute time segment and at each one hour segment up to 24 hours (t=0.5, 1, 2, 3, 4 . . . 24). The calculated area is the accumulated net area from t=0 to t=n. T=0 is the time the subject enters the emergency department.

Modified Method II: Accumulated difference area is calculated at the same time points as Method II; however, the difference area value is indexed for time (i.e. number of measurements). Indexing for number of measurements produces a value which is an average of all $StO_2$ measurements occurring up to t=n. Using this method allows comparison between individuals when the monitored time differs.

Physiological Influences on $StO_2$, that are a) known to affect $StO_2$, and b) have a discrete start and stop time are excluded. An example is the occlusion of blood flow resulting from the use of a tourniquet.

In one embodiment, the present invention is a method of calculating a net tissue oxygenation cumulative area or cumulative ischemia score (CISS) from near continuous tissue hemoglobin oxygen saturation ($StO_2$) measurements.

The integrated or summed product of time (t) or measurement number and $StO_2$ relative to a $StO_2$ threshold limit (STL) provides a cumulative ischemia score for $StO_2$ (CISS) as follows:

$$CISS = \sum_{i=0}^{i=TimeInterval} [t(i+1) - t(i)] \times [\Delta StO_2(i+1) + \Delta StO_2(i)]/2$$

whereas $\Delta StO_2 = StO_2 - STL$ and $STL = StO_2$ threshold limit

Thus CISS represents the product of total measurement time (Time Interval from above) and the average $StO_2$ relative to a $StO_2$ threshold limit. Multiplying CISS by the total measurement time provides average $StO_2$ above or below the $StO_2$ threshold limit. If the $StO_2$ threshold limit is zero, then an absolute average $StO_2$ for the time interval is obtained. Thus for a specified time interval, CISS can alternatively be represented as the average $StO_2$ above or below (relative to) a $StO_2$ threshold limit.

Figure 5:
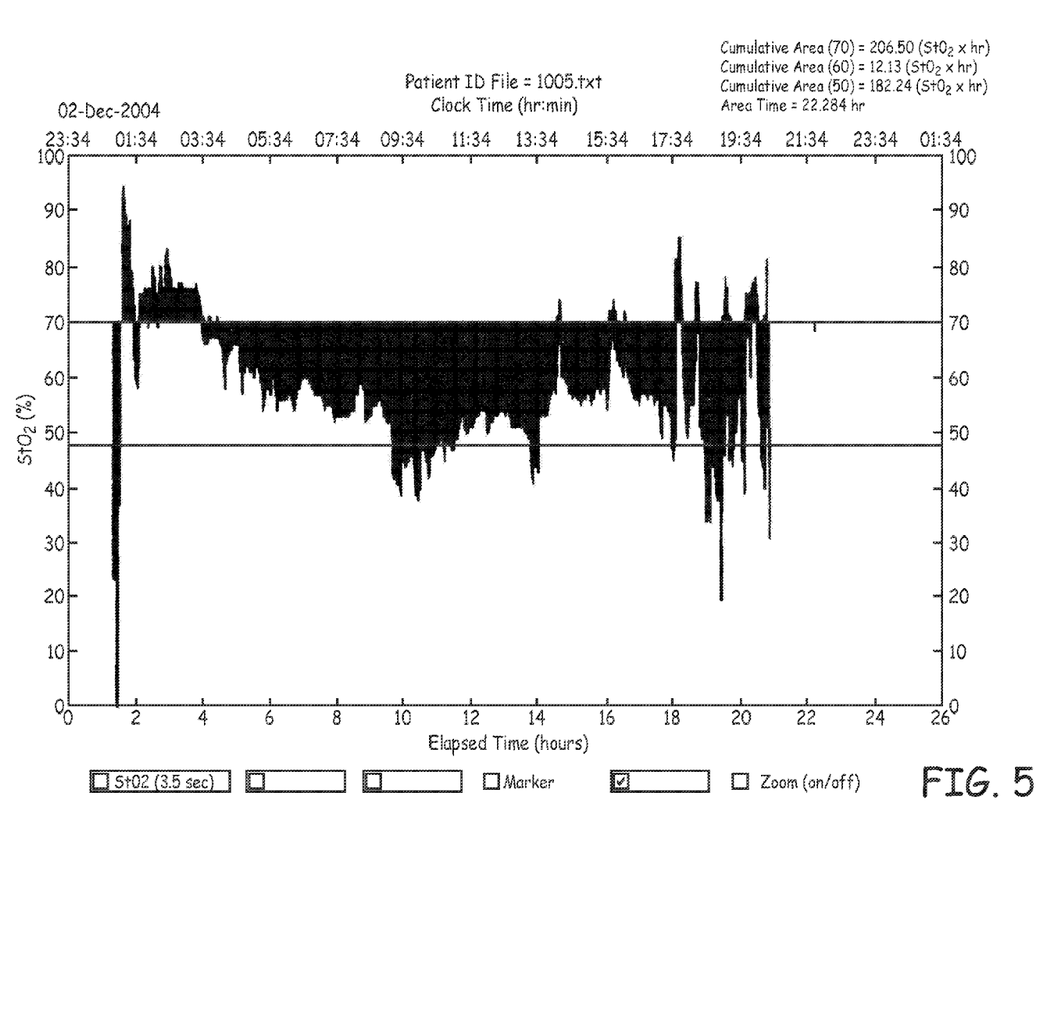
FIG. 5 is a graphical representation of CISS showing a negative cumulative StO$_2$ net area or CISS=−206.5 for a 22 hour monitoring period.

The CISS value may be displayed graphically as in FIGS. 5-8, all showing a $StO_2$ threshold limit of 70. FIG. 5 shows a negative cumulative $StO_2$ net area or CISS=−206.5 for a 22 hour monitoring period. Most of the $StO_2$ area is below the threshold limit of 70. Cumulative net areas for threshold values of 60 and 50 are also depicted in the upper right corner of the graph. This subject has a higher probability of developing an adverse event.

Figure 6:
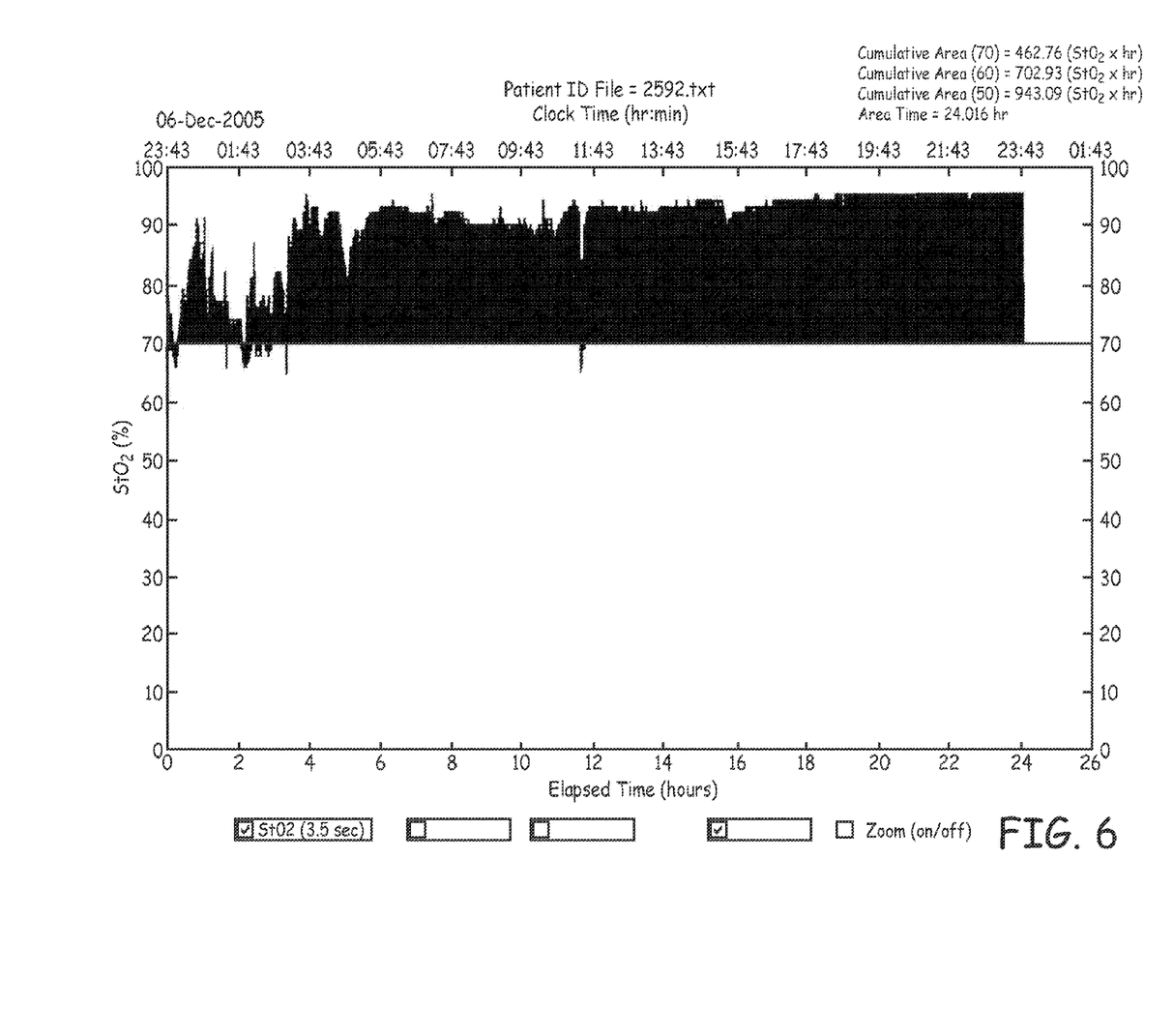
FIG. 6 is a graphical representation of CISS showing a positive cumulative StO$_2$ net area or CISS=463 for a 24 hour monitoring time period.

FIG. 6 shows a positive cumulative $StO_2$ net area or CISS=463 for a 24 hour monitoring time period. Nearly all the $StO_2$ area is above the threshold limit of 70. This subject has lower probability of developing an adverse event.

Figure 7:
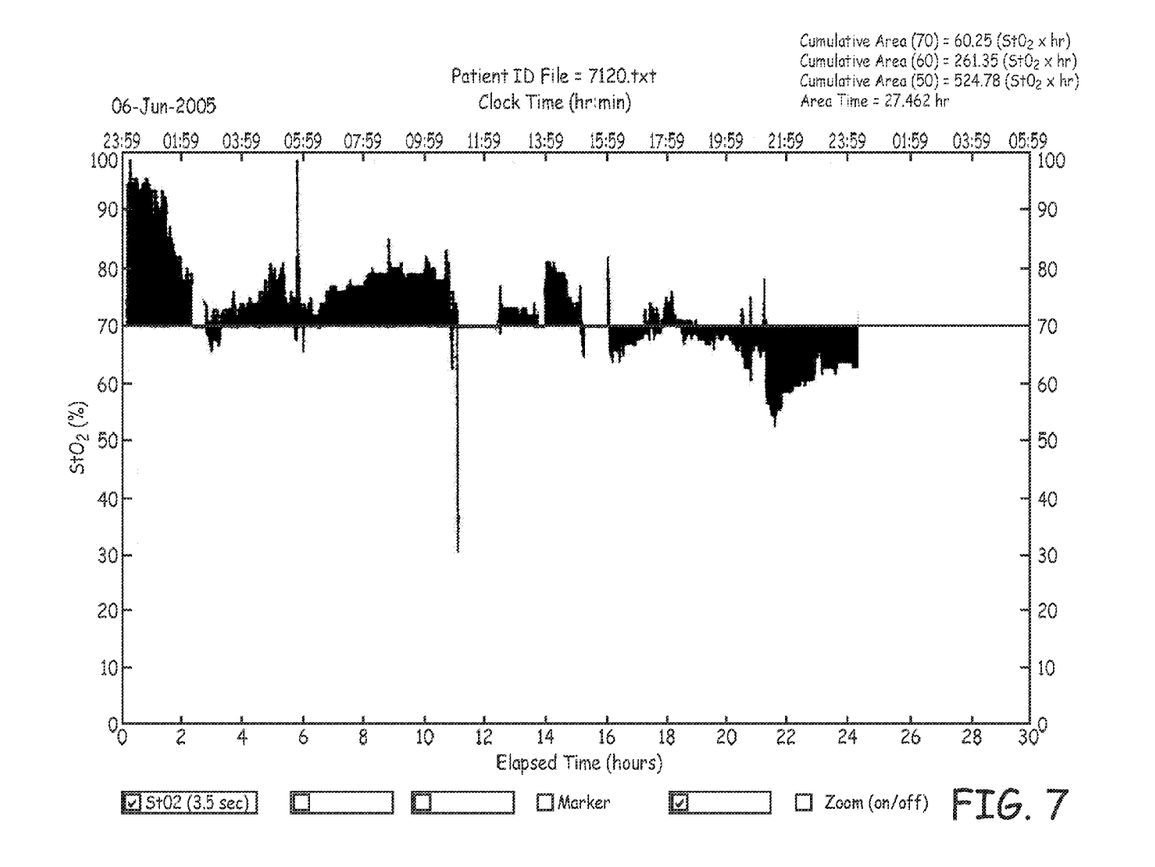
FIG. 7 is a graphical representation of CISS showing that the cumulative StO$_2$ net area is decreasing over a 28 hour time period.

FIG. 7 shows that the cumulative $StO_2$ net area is decreasing over a 28 hour time period. This subject has increasing probability of developing an adverse event.

Figure 8:
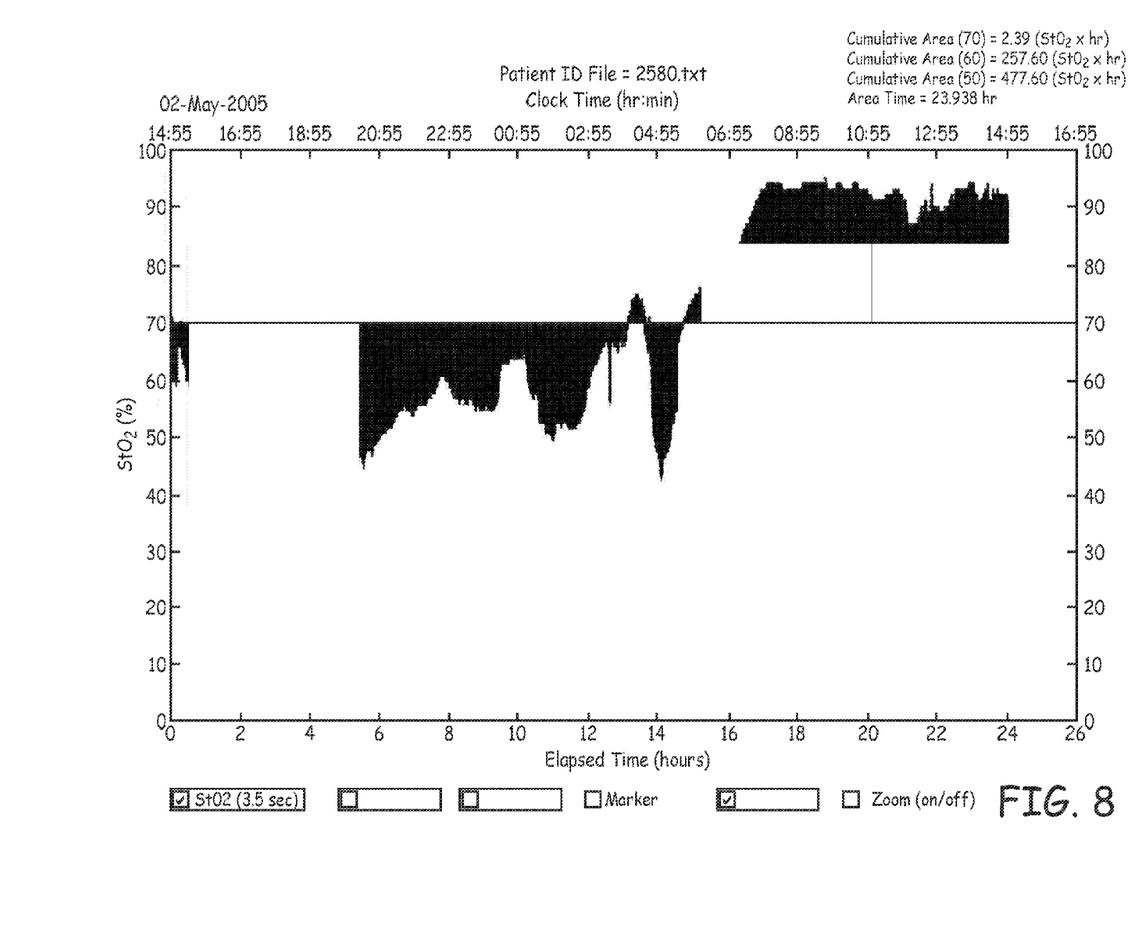
FIG. 8 is a graphical representation of CISS showing that the cumulative StO$_2$ net area or CISS is increasing over a 24 hour time period.

FIG. 8 shows that the cumulative $StO_2$ net area or CISS is increasing over a 24 hour time period. This subject has decreasing probability of developing an adverse event.

To aid in visualization of the cumulative $StO_2$ net area trend, positive area above the threshold and negative area below the threshold could have different colors or fill patterns. An audible or visual alarm associated with the higher probability of an adverse event, decreasing or low CISS or live $StO_2$ below the $StO_2$ threshold limit could warn the user that interventional treatment (such as surgical repair of bleeding or infusion of volume expanding fluids such as blood or saline) may be warranted.

In some embodiments, the CISS is depicted (not shown in FIGS. 5-8) by trending the calculated CISS value(s) (cumulative area values in upper right corner of graphs) over time as the time interval of measurement increases. In this manner, increasing or decreasing CISS magnitude would be more readily apparent to the user as opposed to area visualization shown in FIGS. 5-8.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof. All patents, patent applications and publications are hereby incorporated by reference.

EXAMPLES

The following examples serve to illustrate the present invention. These examples are in no way intended to limit the scope of the invention.

Example 1

$StO_2$ Measurements

The InSpectra $StO_2$ Tissue Oxygenation monitor, which uses infrared spectroscopy was used to directly measure local tissue oxygen saturation ($StO_2$) in the thenar eminence (the muscle at the base of the thumb) with a 15 mm optical probe.

Figure 9:
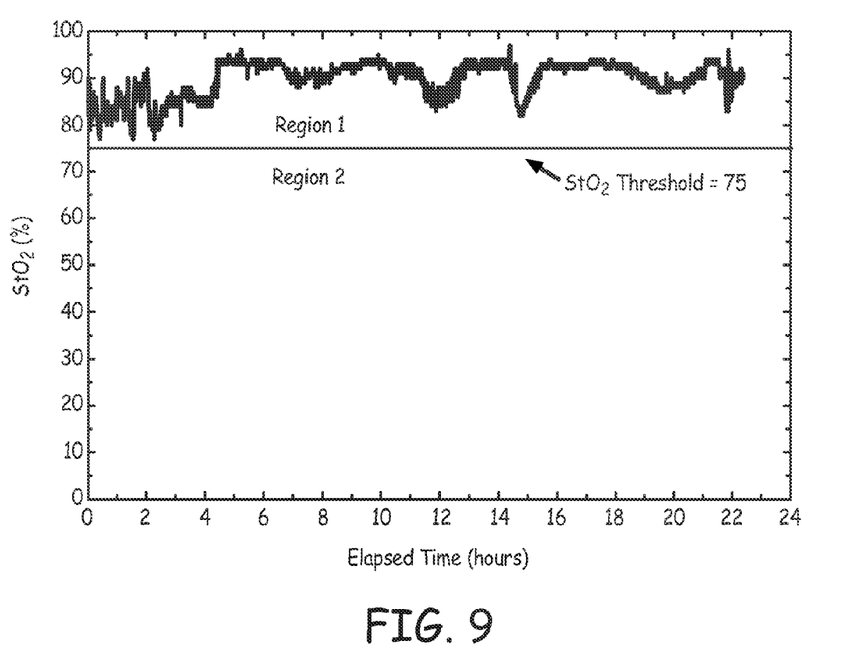
FIG. 9 is a graphical representation of the minimum StO$_2$ value set at a threshold of 75 percent StO$_2$ and showing a normal region (Region 1).

In a prospective study, healthy non-hospitalized subjects were assessed for $StO_2$. A total of 155 subjects were evaluated. Of these 155 subjects, 97.5% of the measurement population had a resting $StO_2$ value of 75 or greater. The minimum observed $StO_2$ value was 72. A $StO_2$ threshold set at or near the minimum observed $StO_2$ value observed in healthy non-hospitalized human subjects defined a Region 1 where $StO_2$ is considered normal (FIG. 9). In this case, a physician or end user would not treat a subject in order to affect or change $StO_2$. The alarm status of a monitoring device which graphically or numerically displays $StO_2$ would be in an off status, such as quiet or non-visually highlighted.

Example 2

Use of $StO_2$ as a Prognostic Indicator in Hypoperfusion

Multiple organ dysfunction syndrome (MODS) was chosen as the indicator of hypoperfusion because early hypoperfusion is generally associated with the later development of organ dysfunction.

In a second prospective clinical study involving 383 severely injured subjects, a minimum observed $StO_2$ below 75 characterized 78% of the subjects developing MODS and 91% of the subjects who died. Subjects that maintained $StO_2$ above 75 within the first hour of emergency department arrival (i.e. minimum $StO_2$ stayed above 75) had an 88% chance of MODS-free survival. A $StO_2$ threshold set at or near the minimum $StO_2$ value associated with a higher risk of bad outcome in hospitalized subjects defines a region (FIG. 10, Region 2) where $StO_2$ is considered abnormal. In this case, a physician or end user may elect to treat a subject in order to affect or change $StO_2$. The alarm status of a monitoring device which graphically or numerically displays $StO_2$ would be in an on status, such as not quiet or visually highlighted.

Figure 10:
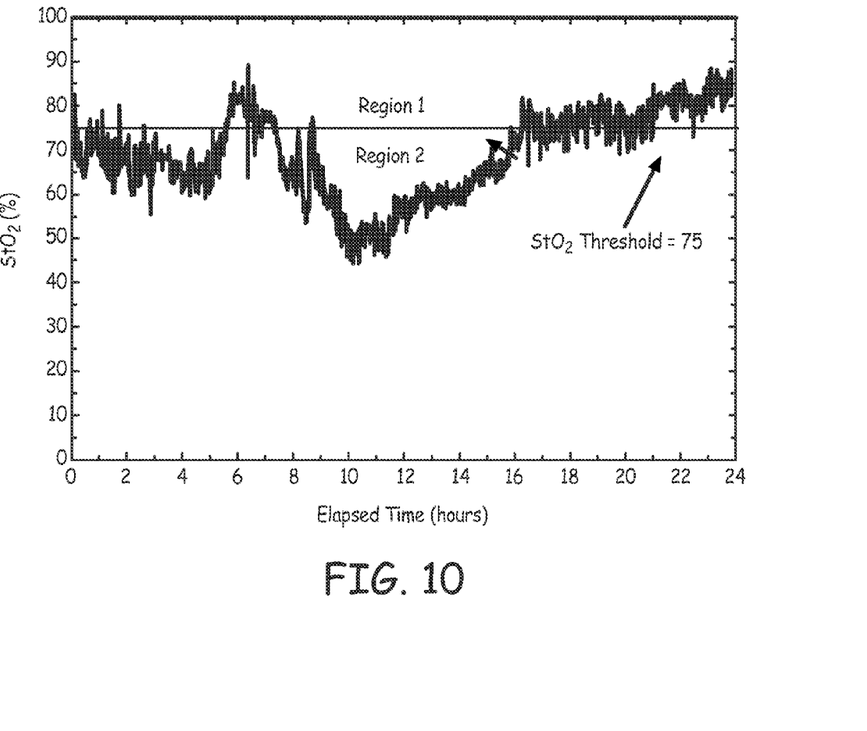
FIG. 10 is a graphical representation of the minimum StO$_2$ value set at a threshold of 75 percent StO$_2$ and showing a region below the threshold associated with higher risk of developing an adverse health outcome.
Figure 11:
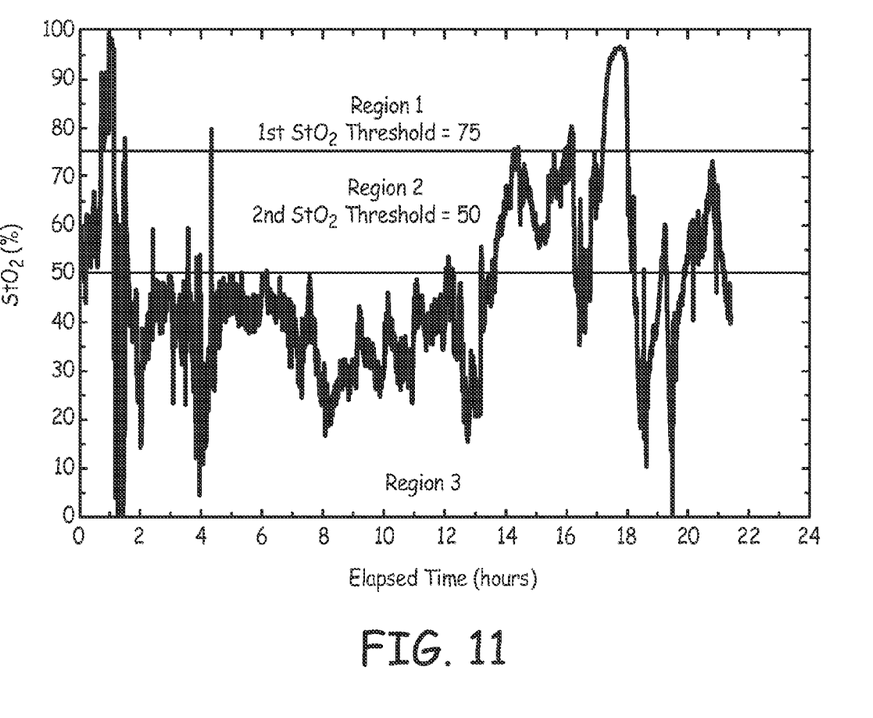
FIG. 11 is a graphical representation of the minimum StO$_2$ value set at a threshold of 75 percent StO$_2$ and showing Region 2 in FIG. 10 divided into two different regions (Regions 2 and 3).

Region 2 of FIG. 10 can be divided into two different regions (Region 2 and 3 of FIG. 11) in order to better define $StO_2$ associated with the highest risk of a bad outcome. In this case, a physician or end user observing $StO_2$ in Region 3 (FIG. 11) would treat a subject in order to affect or change $StO_2$. The Region 3 (FIG. 11) alarm status of a monitoring device which graphically or numerically displays $StO_2$ would be in an on status, such as not quiet or visually highlighted, but distinctively different than the alarm indicator(s) of Region 2 (FIG. 10).

Example 3

Figure 12:
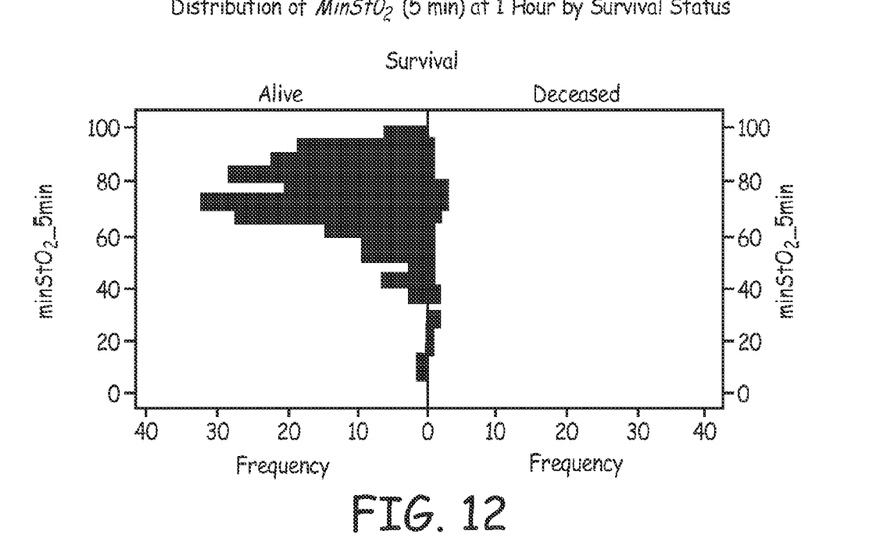
FIG. 12 is a graphical representation of the distribution of MinStO$_2$(5 min) at 1 hour by survival status.

The distributions of the $StO_2$ measure of minimum $StO_2$ ($MinStO_2$) at 1 hour for deceased and surviving subjects are shown in FIG. 12. The interval of 1 hour was chosen based on the high level of association of $StO_2$ measures with survival status seen there and the availability of monitoring data.

Figure 13:
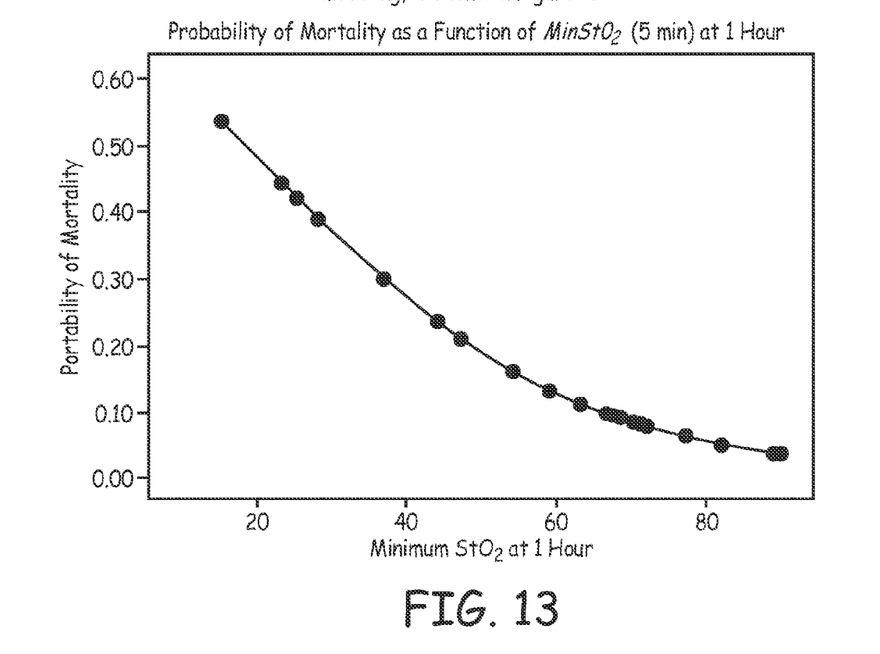
FIG. 13 is a graphical representation of the probability of mortality as a function of MinStO$_2$(5 min) at 1 hour.

The probability of developing MODS as a function of $MinStO_2$ based on logistic regression modeling is shown in FIG. 13.

The invention claimed is:

1. A method for predicting a health status of a subject, comprising:
    measuring the levels of hemoglobin oxygenation ($StO_2$) in tissue of the subject;
    comparing the measured levels to a hemoglobin oxygenation threshold value;
    trending a plurality of $StO_2$ levels over a period of time;
    determining the magnitude of a net tissue oxygenation cumulative area or cumulative ischemia score based on the trended $StO_2$ levels; and
    predicting a change in the health status of the subject from a first health status to a second health status based on the magnitude of the net tissue oxygenation cumulative area or cumulative ischemia score associated with the trended $StO_2$ levels relative to the hemoglobin oxygenation threshold value.

2. The method of claim 1 wherein the measuring of $StO_2$ is measuring on a thenar eminence muscle of a hand.

3. The method of claim 1 wherein the measuring of the $StO_2$ is by spectroscopic radiation.

4. The method of claim 3 wherein the spectroscopic radiation is near infrared radiation.

5. The method of claim 1 wherein the first health status is a lower risk or probability of developing an adverse health outcome.

6. The method of claim 1 wherein the second health status is a higher risk or probability of developing an adverse health outcome.

7. The method of claim 6 wherein the adverse health outcome is ischemia, hypoperfusion, hypoxia, oxygen debt death, multiple organ dysfunction, ventilator-free days or number of hospitalization days.

8. The method of claim 1 wherein the threshold value is a minimum $StO_2$ value.

9. The method of claim 8 wherein the minimum $StO_2$ value is 75 percent.

10. The method of claim 1 wherein the net tissue oxygenation cumulative area or cumulative ischemia score is calculated using the equation:

$$CISS = \sum_{i=0}^{i=TimeInterval} [t(i+1) - t(i)] \times [\Delta StO_2(i+1) + \Delta StO_2(i)]/2.$$

11. The method of claim 1 wherein the threshold value is set by a physician or end user.

12. The method of claim 1 wherein the threshold value of 50 percent $StO_2$ indicates a highest probability of developing an adverse health outcome.

13. An apparatus for predicting a subject's health status based on a measure of hemoglobin oxygen saturation ($StO_2$), comprising:
    a subject interface comprising a light path for irradiating tissue of the subject with spectroscopic radiation and a detector for detecting a spectral response from the tissue responsive to irradiation with the spectroscopic radiation;
    a display for displaying data;
    a memory configured for storing a predetermined hemoglobin oxygenation threshold value or range;
    a processor operatively connected to the memory and the subject interface such that the processor generates data from information comprising the spectral response of the tissue sample in a pre-selected format;

wherein the processor is configured to issue a signal to indicate when a measured StO$_2$ data is outside of the hemoglobin oxygenation threshold value or range; and wherein the processor is configured to trend a plurality of StO$_2$ data measurements taken over a period of time and predict a change in the health status of the subject from a first health status to a second health status based on the magnitude of a net tissue oxygenation cumulative area or cumulative ischemia score associated with the trended StO$_2$ data measurements relative to the hemoglobin oxygenation threshold value or range.

14. The apparatus of claim 13 wherein the subject interface is placed on a thenar eminence.

15. The apparatus of claim 13 wherein the pre-determined threshold value is a minimum StO$_2$.

16. The apparatus of claim 15 wherein the minimum StO$_2$ value limit is 75 percent.

17. The apparatus of claim 15 wherein a threshold of 50 percent StO$_2$ signals a highest probability of developing an adverse health outcome.

18. The apparatus of claim 13 wherein the memory is configured for storing data representative of a correlation which provides the relative concentration of the oxygenated hemoglobin as a function of a scaled, second derivative spectrum value input, wherein the scaled second derivative value input is derived from the spectral response obtained from the tissue sample at a plurality of wavelengths within a wavelength range from 600 nm to 900 nm.

19. The apparatus of claim 13 wherein the apparatus further signals to indicate when StO$_2$ levels are generally trending above or below the threshold value.

20. The apparatus of claim 13 wherein the net tissue oxygenation cumulative area or cumulative ischemia score is calculated using the equation:

$$CISS = \sum_{i=0}^{i=TimeInterval} [t(i+1) - t(i)] \times [\Delta StO_2(i+1) + \Delta StO_2(i)]/2.$$

21. The apparatus of claim 13 wherein a threshold can be adjusted according to the end user.

22. A device for predicting a subject's health status based on a measure of hemoglobin oxygen saturation (StO$_2$), comprising:

means for sensing including a light source assembly for generating spectroscopic radiation for irradiating a tissue and a spectroscopic detector for detecting a spectral response emitted by the tissue sample responsive to irradiation with the spectroscopic radiation;

means for displaying data;

means for providing a notice to a user upon the occurrence of a specified event;

means for storing, said means for storing including a pre-determined hemoglobin oxygenation threshold value or range;

a means for generating data of the tissue sample from information comprising the spectral response of the tissue sample;

a means for characterizing the data in a pre-selected form including a control system interfaced with the means for storing and the means for sensing such that the control system generates data of the tissue sample;

a means to indicate when a measured StO$_2$ data is outside of the pre-determined hemoglobin oxygenation threshold value or range; and a means for trending a plurality of StO$_2$ data measurements taken over a period of time and predicting a change in the health status of the subject from a first health status to a second health status based on the magnitude of a net tissue oxygenation cumulative area or cumulative ischemia score associated with the trended StO$_2$ data measurements relative to the hemoglobin oxygenation threshold value or range.

23. A method of determining a relationship between hemoglobin oxygenation (StO$_2$) and a health status of a subject, the method comprising;

monitoring the subject's StO$_2$ for a period;

storing the subject's StO$_2$ measurements versus time to form a StO$_2$ curve;

determining an area between the StO$_2$ curve and a hemoglobin oxygenation threshold value;

predicting whether the subject is likely to develop a first health status if the area is above the threshold value or generally trending above the threshold value, or likely to develop a second health status if the area is below the threshold value or generally trending below the threshold value; and wherein the relationship between the StO$_2$ and the health status is determined based on the magnitude of a net tissue oxygenation cumulative area or cumulative ischemia score relative to the hemoglobin oxygenation threshold value.

24. The method of claim 23 wherein the first health status is a lower risk or probability of developing an adverse health outcome.

25. The method of claim 23 wherein the second health status is a higher risk or probability of developing an adverse health outcome.

26. The method of claim 23 wherein the threshold value is a minimum StO$_2$ value.

27. The method of claim 26 wherein the minimum StO$_2$ value is 75 percent.

28. The method of claim 23 wherein the net tissue oxygenation cumulative area or cumulative ischemia score is calculated using the equation:

$$CISS = \sum_{i=0}^{i=TimeInterval} [t(i+1) - t(i)] \times [\Delta StO_2(i+1) + \Delta StO_2(i)]/2.$$

29. The method of claim 23 wherein the threshold value is pre-set by a user.

30. The method of claim 23 wherein a physician or end-user treats the subject to affect or change the StO$_2$ depending on the health status of the subject.

31. The method of claim 23 wherein the storing is storing StO$_2$ in the form of graphs.

* * * * *